United States Patent [19]

Elion et al.

[11] 4,038,479
[45] July 26, 1977

[54] AMINO PURINE DERIVATIVES

[75] Inventors: Gertrude B. Elion, Bronxville, N.Y.; Robert A. Strelitz, Edison, N.J.

[73] Assignee: Burroughs Wellcome Co., Research Triangle Park, N.C.

[21] Appl. No.: 178,406

[22] Filed: Sept. 7, 1971

Related U.S. Application Data

[62] Division of Ser. No. 877,443, Nov. 17, 1969, Pat. No. 3,666,856.

[51] Int. Cl.$^2$ .......................................... C07H 19/16
[52] U.S. Cl. ..................................... 536/24; 424/180
[58] Field of Search ................... 260/211.5 R; 536/24; 424/180

[56]  References Cited

U.S. PATENT DOCUMENTS

| | | | |
|---|---|---|---|
| 2,719,843 | 10/1955 | Davoll et al. | 260/211.5 R |
| 3,225,029 | 12/1965 | Yamaoka | 260/211.5 R |
| 3,269,917 | 8/1966 | Imada et al. | 260/211.5 R |
| 3,298,923 | 1/1967 | Banno et al. | 260/211.5 R |
| 3,498,970 | 3/1970 | Yamada et al. | 260/211.5 R |
| 3,590,029 | 6/1971 | Koch et al. | 260/211.5 R |
| 3,703,507 | 11/1972 | Haskell et al. | 260/211.5 R |

FOREIGN PATENT DOCUMENTS 1,070,413  6/1967  United Kingdom .......... 260/211.5 R Primary Examiner—Johnnie R. Brown
Attorney, Agent, or Firm—Donald Brown

[57]  ABSTRACT

Compounds of the formula

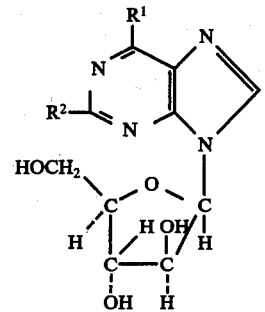

where $R^1$ is amino or lower alkylamino, $R^2$ is amino or hydrogen and pharmaceutically acceptable salts thereof, provided that when $R^1$ is amino, $R^2$ is amino. The compounds are useful as immune suppressants and as antivirals.

2 Claims, No Drawings

AMINO PURINE DERIVATIVES

This is a division, of application Ser. No. 877,443, filed Nov. 17, 1969 now U.S. Pat. No. 3,666,856.

This invention relates to purine sugar derivatives which are useful as suppressors of the immune response and as antiviral agents.

The compounds of this invention are of the formula (I)

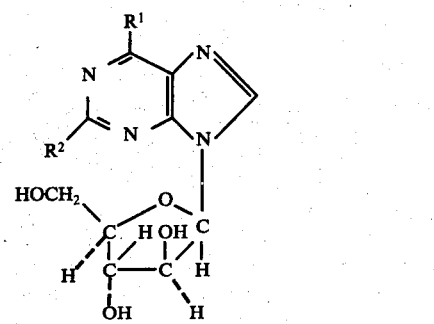

where $R^1$ is amino or lower alkyl amino, $R^2$ is amino or hydrogen, provided that whenever $R^1$ is amino, $R^2$ is amino.

In the above, lower alkyl is defined as having 1 to 4 carbon atoms (i.e. methyl, ethyl, propyl, and butyl).

The compounds of this invention may also be provided as salts and be used in pharmacological and medical applications as pharmaceutically acceptable salts, although it should be understood that the activity of any salt administered or used medically resides in the base. In addition, toxic salts can be made and converted to either the base or pharmaceutically acceptable salts by standard decomposition methods.

Salts which are especially preferred for therapeutic use are salts of pharmaceutically acceptable carboxylic acids which as lactic, acetic, malic as well as salts of pharmaceutically acceptable weak mineral acids.

The compounds of formula I and their pharmaceuticaly acceptable salts are particularly useful in treating viral infections resulting from DNA viruses, of which vaccinia and herpes are examples.

For viral infections of the eye or other external tissues such as caused by the above viruses the compounds of Formula I or their pharmaceutically acceptable salts would preferably be applied to the infected part of the body of the patient as a topical ointment. The compounds of this invention are also useful in treating systemic vaccinial and herpes viral infections and for such use, the compounds are preferably administered orally or parenterally.

The compounds of Formula I or their pharmaceuticaly acceptable salts are also useful to suppress the immune response of an animal to the transplant of foreign cells into the body of the animal. The compunds of Formula I or their pharmaceutically acceptable salts are also useful in the treatment of autoimmune diseases in mammals such as Lupus Erythematosis, Hemolytic anemia, Ulcerative Colitis and Nephrosis.

The compunds of this invention are preferably used internally (orally or parenterally) for the treatment of viral infections at dose levels (as base) at about 1–100 mg./kg. of mammal bodyweight, and is preferably used in man in a unit dosage form (administered a few times daily) in the amount of 10 to 250 mg. per unit depending on the patient being treated. For use as an ointment, the amount used would be about one half of that used for internal use.

For use as immune surpressants, the compounds of Formula I, are administered internally at dosages preferrably of about 3 to 10 mg./kg. of mammal body weight.

Of the compounds of Formula I, the compound where $R^1$ and $R^2$ are both amino, is the most preferred, particularly for its extremely high antiviral activity. This compound, 2,6-diamino-9-($\beta$-D-arabinofuranosyl) purine has in tests been found to be an extremely effective as an antiviral agent, as for example, against the herpes virus. In particular, mice infected intracerebrally with 100 $LD_{50}$ of herpes virus were injected subcutaneously with 1 mg. (50 mg./kg.) 2,6-diamino-9-($\beta$-D-arabinofuranosyl) purine (twice daily to a total of five doses. The injection is preferably a solution of the compound in a sterile fluid, i.e. water since the compound is readily soluble. After five doses, in comparison with five untreated controls, a hundred percent of the treated mice survived at least five days without clinical signs of infection, whereas 60% of the controls died, and the two remaining controls were moribund after five days.

The compound 2,6-diamino-9-($\beta$-D-arabinofuranosyl) purine has also shown substantial and unexpectedly high activity against vaccina virus. Five mice injected intracerebrally with 100 $LD_{50}$ of Vaccina virus were given the compound subcutaneously in a dose of 1 mg.(50 mg./kg.) twice a day. In comparison with a control group of five injected but untreated mice, sixty percent survival were achieved with the treated mice, while all the mice of the control group died within 4½ days.

Experiments have also shown that the preferred compound of this invention 2,6-diamino-9-($\beta$-D-arabinofuranosyl) purine is unexpectedly useful in suppressing the immune response to transplanted cells. We have been able to demonstrate the immunosuppresive activity of this preferred compound against antibodies generated upon the transplant of cells into mammals (i.e. mice).

For use as an antiviral, the compound 2,6-diamino-9-($\beta$-D-arabinofuranosyl) purine or its salts may be given parenterally (in an injectable solution, orally (tablets or capsules), used as a suppository, applied as an optic solution, or applied topically as an ointment, cream, powder, etc., as a pharmaceutical preparation in accordance with known medical or veterinarial practice. The preferred compound is preferably administered at a dosage of about 1 to 100 mg./kg. of mammal body weight (i.e. mice, rats, dogs, humans). In a unit dosage the compound is preferably administered at a dosage of about 10–250 mg. per unit dose which is preferably given or used a few (2-4) times daily. For external usage the dosage is preferably one half the dosage given above, i.e. 5 to 50 mg./kg. or 5–125 mg. per unit dose. For use in the treatment of autoimmune conditions or in immunosuppressive applications, the preferred drug or compound is preferably given orally and at a dose level of about 3 to 10 mg/kg. of mammal body weight a few times daily.

The compounds of Formula I may be conveniently prepared by reducing (i.e. by catalytic hydrogenation) the compound of Formula II.

(II)

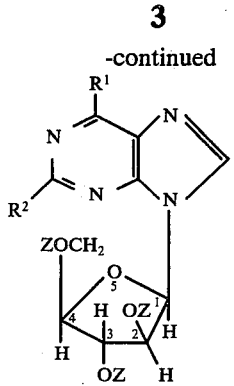

(II)

where $R^1$ and $R^2$ is as defined previously above, to prepare the corresponding compound of formula I. Z is a blocking group such that when attached to the oxygen atom at position 2 the sugar moiety, there is no interference with processes at carbon No. 1 of the sugar. For such purposes acyl is not acceptable as Z but alkyl is. A further limitation is that Z should be removable, when desired, under mild conditions. The benzyl group satisfied both requirements and is preferred. Others that can be used are p-phenylbenzyl and α and β-menaphthyl. The reduction may be accomplished catalytically, i.e. by use of a hydrogenation catalyst such as palladium, palladized charcoal, platinum black, Raney nickel, or by reacting the compound of Formula II with a reducing agent such as sodium in liquid ammonia. Potassium and other alkali metals may also be used.

The preferred compound ($R^1=R^2=NH_2$) of Formula I is preferably made by the following sequence of steps. A compound of Formula III where $X^1$ and $X^2$ is halogen, preferably chlorine or bromine and Z is a blocking group as defined above, preferably benzyl is reacted as follows:

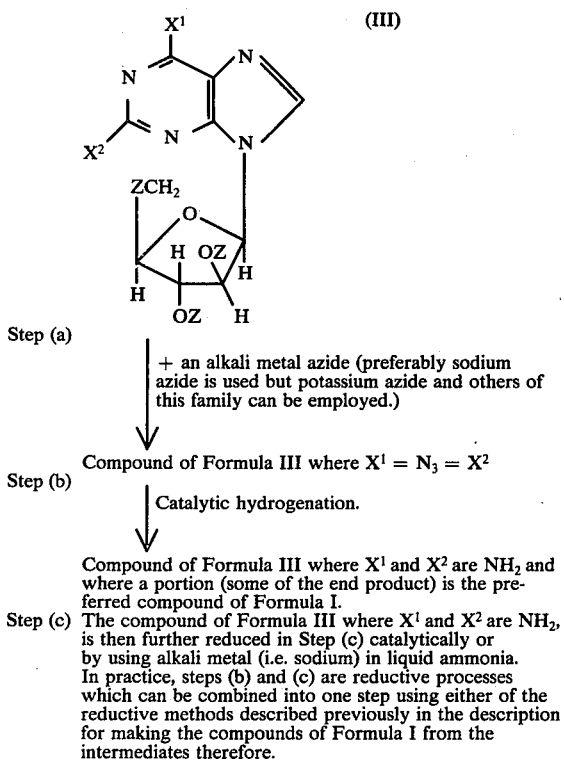

Step (a)

+ an alkali metal azide (preferably sodium azide is used but potassium azide and others of this family can be employed.)

Step (b) Compound of Formula III where $X^1 = N_3 = X^2$

Catalytic hydrogenation.

Compound of Formula III where $X^1$ and $X^2$ are $NH_2$ and where a portion (some of the end product) is the preferred compound of Formula I.

Step (c) The compound of Formula III where $X^1$ and $X^2$ are $NH_2$, is then further reduced in Step (c) catalytically or by using alkali metal (i.e. sodium) in liquid ammonia. In practice, steps (b) and (c) are reductive processes which can be combined into one step using either of the reductive methods described previously in the description for making the compounds of Formula I from the intermediates therefore.

Thus the present invention provides the above methods of preparation of the compound of Formula I and the preferred compound $R^1$ and $R^2=NH_2$ and acid addition salts thereof.

This invention also provides pharmaceutical compositions or preparations comprising a compound of Formula I or a pharmaceutically acceptable salt thereof and a pharmaceutically acceptable carrier therefore. The compositions may be used orally, parenterally, or topically depending on whether the preparation is used to treat internal or external viral infections caused by DNA viruses.

It is preferably administered orally or as a solution (injection) when it is an immune or autoimmunal response suppressant.

This invention also provides a method for treating viral infections caused by DNA viruses in mammals, (i.e. mice, rats, dogs, man etc.) by administering an effective non-toxic antiviral amount of a compound of Formula I (preferably where $R^1=R^2=NH_2$) or a salt thereof to the infected mammal. DNA viruses are those viruses which utilize DNA as building blocks.

The invention also provides novel and useful compounds of the above formulas.

For oral administration, fine powders or granules of the compounds may contain diluting, dispersing and/or surface active agents, and may be presented in a draft, in water or in a syrup, in capsules or cachets in the dry state or a non-aqueous suspension wherein suspending agents may be included; in tablets, when binders and lubricants may be included; or in a suspension in water or a syrup.

Where desirable or necessary flavoring, preserving, suspending, thickness or emulsifying agents can be included. Tablets and granules are preferred, and these may be coated. For parenteral administration, the compounds may be presented in aqueous injection solutions which may contain antioxidants, buffers etc.

The following examples illustrate the invention:

EXAMPLE I 2,6-Diazido-9-(2,3,5-tri-O-benzyl-β-D-arabinofuranosyl) purine(I)

A solution of 2.1 g. of 2,6-dichloro-9-(2,3,5-tri-O-benzyl-β-D-arabinofuranoxyl)purine (Keller et al., J. Org. Chem., 32, 1644 [1967]) in 8 ml. of methanol and 2 ml. of acetone was heated with 440 mg. (2 molecular equivalents) of sodium azide for 6 hours under reflux conditions. The precipitated sodium chloride was filtered off, and the yellow filtrate, containing the 2,6-diazido-9-(2,3,5-tri-O-benzyl-β-D-arabinofuranosyl) purine showed absorption maxima at 245,270 (shoulder), 300 mu in 95% ethanol. The filtrate was used directly for the reduction in the next step.

EXAMPLE II 2,6-Diamino-9-(2,3,5-tri-O-benzyl-β-D-arabinofuranosyl)purine(II)

The reaction product (I) was reduced with a 5% palladium charcoal catalyst and hydrogen at 2 atmospheres of pressure at 25° C. After 4 hours, the catayst was removed and the filtrate was evaporated to dryness under reduced pressure. The residue (1.88 g.) was recrystallized from 95% ethanol to give 1.0 g. of pale yellow crystals, m.p. 158°-159°, which was homogenous on thin-layer chromatography. The analysis corresponded to 2,6-diamino-9-(2,3,5-tri-O-benzyl-β-D-arabinofuranosyl)purine.

EXAMPLE III

2,6-Diamino-9-(β-D-arabinofuranosyl)purine

To 1 g. of product II was added 200 ml. of liquid ammonia. Small pieces of sodium were added until the blue color persisted for several minutes. A total of 350 mg. of sodium was used. The bluecolor was discharged with a few crystals of ammonium chloride. The ammonia was evaporated under a stream of nitrogen and the residue was triturated with 50 ml. of benzene. The insoluble residue was taken up in a few ml. of water and neutralized with acetic acid. The product (500 mg.), after recrystallization from water, melted at 257°-259° with decomposition. The 2,6-diamino-9-(β-D-arabinofuranosyl)purine showed aλmax=253,290 mu at pH 1, and λmax=257, 279 mu at pH 11.

What is claimed is:

1. 2,6-diamino-9-(β-D-arabinofuramosyl)purine.
2. A pharamaceutically acceptable shaft of 2,6-diamino-9-(β-D-arabinofuranosyl)purine.

UNITED STATES PATENT AND TRADEMARK OFFICE
CERTIFICATE OF CORRECTION

PATENT NO. : 4,038,479

DATED : JULY 26, 1977

INVENTOR(S) : GERTRUDE B. ELION and ROBERT A. STRELITZ

It is certified that error appears in the above—identified patent and that said Letters Patent are hereby corrected as shown below:

CLAIM 2, line 1, after "acceptable" please delete "shaft" and insert -- salt --.

Signed and Sealed this

Twenty-fifth Day of October 1977

[SEAL]

Attest:

RUTH C. MASON
*Attesting Officer*

LUTRELLE F. PARKER
*Acting Commissioner of Patents and Trademarks*